US006232316B1

(12) United States Patent
Dull et al.

(10) Patent No.: US 6,232,316 B1
(45) Date of Patent: May 15, 2001

(54) METHODS FOR TREATMENT OF CNS DISORDERS

(75) Inventors: Gary Maurice Dull, Lewisville; William Scott Caldwell, Winston-Salem; Patrick Michael Lippiello, Lewisville; Merouane Bencherif, Winston-Salem, all of NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/098,133

(22) Filed: Jun. 16, 1998

(51) Int. Cl.[7] .................................................. A61K 31/505
(52) U.S. Cl. ............................................................ 514/256
(58) Field of Search ..................... 514/256, 277, 514/345, 348, 349, 351

(56) References Cited

U.S. PATENT DOCUMENTS

| | | |
|---|---|---|
| 4,927,838 | 5/1990 | Guthrie et al. . |
| 5,212,188 | 5/1993 | Caldwell et al. . |
| 5,585,388 | 12/1996 | Cosford et al. . |
| 5,597,919 | 1/1997 | Dull et al. . |
| 5,604,231 | 2/1997 | Smith et al. . |
| 5,616,707 | 4/1997 | Crooks et al. . |
| 5,616,716 | 4/1997 | Dull et al. . |
| 5,663,356 | 9/1997 | Ruecroft et al. . |
| 5,726,316 | 3/1998 | Crooks et al. . |
| 5,731,314 | 3/1998 | Bencherif et al. . |
| 5,811,442 | 9/1998 | Bencherif et al. . |
| 5,824,692 | 10/1998 | Lippiello et al. . |
| 5,861,423 | 1/1999 | Caldwell et al. . |
| 5,885,998 * | 3/1999 | Bencherif et al. .................... 514/256 |

OTHER PUBLICATIONS

Cooper, Donald A. et al., *Biological Mass Spectrometry*, vol. 22, (1993).
Loffler, Karl et al., *Chem. Ber.*, vol. 42, pp. 3431–3438 (1909).
LaForge, F. B., *J. Am. Chem. Soc.*, vol. 50, pp. 2477–2483 (1928).
Pinner, A., *Chem. Ber.*, pp. 2861–2870 (1894).
Malek, N. et al., *J. Org. Chem.*, vol. 47, pp. 5395–5397 (1982).
Joyce, N. J. et al., *Heterocycles*, vol. 29, No. 7, pp. 2947–2949 (1978).
Frank, W. et al., *J. Org. Chem.*, vol. 43(15), pp. 2947–2949 (1978).
Sprouse, C. et al., Abstracts of Papers, p. 32, Coresta/TCRC, Joint Conference (1972).
Pinner, A., *Chem. Ber.*, pp. 1053–1061 (1894).
Acheson, R. et al., *J. Chem. Soc. Perkin Trans.*, vol. 2, pp. 579–585 (1980).
Bleicher, Leo et al., *Synlett*, pp. 1115–1116 (1995).
Lippiello, P. et al., *JPET*, vol. 279, No. 3, pp. 1422–1429 (1996).
Bencherif, M. et al., *JPET*, vol. 279, pp. 1413–1421 (1996).

* cited by examiner

*Primary Examiner*—Russell Travers
*Assistant Examiner*—Shengjun Wang
(74) *Attorney, Agent, or Firm*—Myers Bigel Sibley & Sajovec, P.A.

(57) ABSTRACT

Pharmaceutical compositions incorporate aryl substituted olefinic amine compounds. Representative compounds are (4E)-N-methyl-5-(3-pyridyl)-4-penten-2-amine, (4E)-N-methyl-5-(5-pyrimidinyl)-4-penten-2-amine, (4E)-N-methyl-5-(5-methoxy-3-pyridyl)-4-penten-2-amine, (4E)-N-methyl-5-(6-amino-5-methyl-3-pyridyl)-4-penten-2-amine, (2R)-(4E)-N-methyl-5-(3-pyridyl)-4-penten-2-amine, (2R)-(4E)-N-methyl-5-(5-isopropoxy-3-pyridyl)-4-penten-2-amine, (4E)-N-methyl-5-(5-bromo-3-pyridyl)-4-penten-2-amine, (4E)-N-methyl-5-(5-ethoxy-3-pyridyl)-4-penten-2-amine, (2S)-(4E)-N-methyl-5-(3-pyridyl)-4-penten-2-amine, (4E)-N-methyl-5-(5-isopropoxy-3-pyridyl)-4-penten-2-amine and (2S)-(4E)-N-methyl-5-(5-isopropoxy-3-pyridyl)-4-penten-2-amine.

9 Claims, No Drawings

METHODS FOR TREATMENT OF CNS DISORDERS

BACKGROUND OF THE INVENTION

The present invention relates to pharmaceutical compositions, and particularly pharmaceutical compositions incorporating compounds that are capable of affecting nicotinic cholinergic receptors. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221: 91–96 (1982) and Hamon, *Trends in Pharmacol. Res.* 15:36.

Various nicotinic compounds have been reported as being useful for treating a wide variety of conditions and disorders. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience (1997)*, Holladay et al., *J. Med. Chem* 40(28): 4169–4194 (1997), Bannon et al., *Science* 279: 77–80 (1998), PCT WO 94/08992, PCT WO 96/31475, and U.S. Pat. Nos. 5,583,140 to Bencherif et al., 5,597,919 to Dull et al., 5,604,231 to Smith et al. and 5,616,716 to Dull et al. Nicotinic compounds are reported as being particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to affect the functioning of the CNS, but which compound when employed in an amount sufficient to affect the functioning of the CNS, does not significantly affect those receptor subtypes which have the potential to induce undesirable side effects (e.g., appreciable activity at skeletal muscle and ganglia sites).

SUMMARY OF THE INVENTION

The present invention relates to aryl substituted olefinic amine compounds. Representative compounds are (4E)-N-methyl-5-(3-pyridyl)-4-penten-2-amine, (4E)-N-methyl-5-(5-pyrimidinyl)-4-penten-2-amine, (4E)-N-methyl-5-(5-methoxy-3-pyridyl)-4-penten-2-amine, (4E)-N-methyl-5-(6-amino-5-methyl-3-pyridyl)-4-penten-2-amine, (2R)-(4E)-N-methyl-5-(3-pyridyl)-4-penten-2-amine, (2R)-(4E)-N-methyl-5-(5-isopropoxy-3-pyridyl)-4-penten-2-amine, (4E)-N-methyl-5-(5-bromo-3-pyridyl)-4-penten-2-amine, (4E)-N-methyl-5-(5-ethoxy-3-pyridyl)-4-penten-2-amine, (2S)-(4E)-N-methyl-5-(3-pyridyl)-4-penten-2-amine, (4E)-N-methyl-5-(5-isopropoxy-3-pyridyl)-4-penten-2-amine and (2S)-(4E)-N-methyl-5-(5-isopropoxy-3-pyridyl)-4-penten-2-amine. The present invention also relates to methods for synthesizing certain aryl substituted olefinic amine compounds, such as the compounds of the present invention. Of particular interest are isolated enaniomeric compounds (i.e., compounds in a substantially pure form, as opposed to racemic mixtures), and methods for synthesizing such enaniomeric compounds in substantially pure form.

The present invention also relates to methods for the prevention or treatment of a wide variety of conditions or disorders, and particularly those disorders characterized by dysfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastrointestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds of the formula:

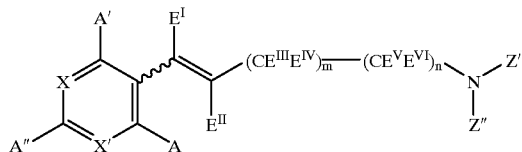

where each of X and X' are individually nitrogen or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., *Chem. Rev.* 91:165 (1991); m is an integer and n is an integer such that the sum of m plus n is 1, 2, 3, 4, 5, 6, 7, or 8, preferably is 1, 2, or 3, and most preferably is 2 or 3; the wavy line in the structure indicates that the compound can have the cis (Z) or trans (E) form; $E^I$, $E^{II}$, $E^{III}$, $E^{IV}$, $E^V$ and $E^{VI}$ individually represent hydrogen or lower alkyl (e.g., straight chain or branched alkyl including $C_1-C_8$, preferably $C_1-C_5$, such as methyl, ethyl, or isopropyl) or halo substituted lower alkyl (e.g., straight chain or branched alkyl including $C_1-C_8$, preferably $C_1-C_5$, such as trifluoromethyl or trichloromethyl), and at least one of $E^I$, $E^{II}$, $E^{III}$, $E^{IV}$, $E^V$ and $E^{VI}$ is non-hydrogen and the remaining $E^I$, $E^{II}$, $E^{III}$, $E^{IV}$, $E^V$ and $E^{VI}$ are hydrogen; and Z' and Z" individually represent hydrogen or lower alkyl (e.g., straight chain or branched alkyl including $C_1-C_8$, preferably $C_1-C_5$, such as methyl, ethyl, or isopropyl), and preferably at least one of Z' and Z" is hydrogen, and most preferably Z' is hydrogen and Z" is methyl; alternatively Z' is hydrogen and Z" represents a ring structure (cycloalkyl or aromatic), such as cyclopropyl, cyclobutyl, cyclopentyl, cyclohexyl, cycloheptyl, adamantyl, quinuclidinyl, pyridyl, quinolinyl, pyrimidinyl, phenyl, benzyl (where any of the foregoing can be suitably substituted with at least one substituent group, such as alkyl, halo, or amino substituents); alternatively Z', Z", and the associated nitrogen atom can form a ring structure such as aziridinyl, azetidinyl, pyrollidinyl, piperidinyl, quinuclidinyl, piperazinyl, or morpholinyl. More specifically, X and X' include N, C—H, C—F, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' where R' and R" are individually hydrogen or lower alkyl (e.g., $C_1-C_{10}$ alkyl, preferably $C_1-C_5$ alkyl, and more preferably methyl, ethyl, isopropyl or isobutyl), an aromatic group-containing species or a substituted aromatic group-containing species, and q is an integer from 1 to 6. R' and R" can be straight chain or branched alkyl, or R' and R" can form a cycloalkyl functionality (e.g., cyclopropyl cyclobutyl, cyclopentyl, cyclohexyl, cycloheptyl, adamantyl, and quinuclidinyl). Representative aromatic group-containing species include pyridyl, quinolinyl, pyrimidinyl, phenyl, and benzyl (where any of the foregoing can be suitably substituted with at least one substituent group, such as alkyl, halo, or amino substituents). Other representative aromatic ring systems are set forth in Gibson et al., *J. Med. Chem.* 39:4065 (1996). When X and X' represent a carbon atom bonded to a substituent species, that substituent species often has a sigma m value which is between about −0.3 and about 0.75, and frequently between about −0.25 and about 0.6. In certain circumstances the substituent species is characterized as having a sigma m value not equal to 0. A, A' and A" individually represent those species described as substituent species to the aromatic carbon atom previously described for X and X'; and usually include hydrogen, halo (e.g., F, Cl, Br, or I), alkyl (e.g., lower straight chain or branched $C_{1-8}$ alkyl, but preferably methyl or ethyl), or NX"X"' where X" and X"' are individually hydrogen or lower alkyl, including $C_1-C_8$, preferably $C_1-C_5$ alkyl. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. In a preferred embodiment, m is 1 or 2, n is 1, $E^I$, $E^{II}$, $E^{III}$, $E^{IV}$ and $E^{VI}$ each are hydrogen, and $E^V$ is alkyl (e.g., methyl). Depending upon the identity and positioning of each individual $E^1$, $E^{II}$, $E^{III}$, $E^{IV}$, $E^V$ and $E^{VI}$, certain compounds can be optically active. Additionally, compounds of the present invention can have chiral centers within the alkenyl side chain e.g., the compound can have an R or S configuration depending on the selection of a $E^{III}$, $E^{IV}$, $E^V$ and $E^{VI}$, with the S configuration being preferred. Depending upon $E^1$, $E^{II}$, $E^{III}$, $E^{IV}$, $E^V$ and $E^{VI}$, compounds of the present invention have chiral centers, and the present invention relates to racemic mixtures of such compounds as well as enaniomeric compounds. Typically, the selection of m, n, $E^I$, $E^{II}$, $E^{III}$, $E^{IV}$, $E^V$ and $E^{VI}$ is such that up to about 4, and frequently up to 3, and usually 1 or 2, of the substituents designated as $E^I$, $E^{II}$, $E^{III}$, $E^{IV}$, $E^V$ and $E^{VI}$ are non-hydrogen substituents (i.e., substituents such as lower alkyl or halo-substituted lower alkyl). Typically, X is CH, CBr or COR. Most preferably, X' is nitrogen.

Of particular interest are compounds of the formula:

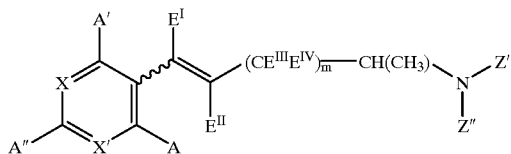

where, m, $E^I$, $E^{II}$, $E^{III}$, $E^{IV}$, X, Z', Z", A, A' and A" are as defined hereinbefore.

Representative compounds of the present invention are (3E) and (3Z)-N-methyl-4-(3-pyridyl)-2-methyl-3-buten-1-amine, (3E) and (3Z)-N-methyl-4-(3-pyridyl)-3-methyl-3-buten-1-amine, (5E) and (5Z)-N-methyl-6-(3-pyridyl)-5-hexen-3-amine, (4E) and (4Z)-N-methyl-5-(3-pyridyl)-2-methyl-4-penten-2-amine, (4E) and (4Z)-N-methyl-5-(3-pyridyl)-3-methyl-4-penten-2-amine, (4E) and (4Z)-N-methyl-5-(3-pyridyl)-4-penten-2-amine, (4E) and (4Z)-N-methyl-5-(3-pyridyl)-1,1,1-trifluoro-4-penten-2-amine, (4E) and (4Z)-N-methyl-5-(3-pyridyl)-4-methyl-4-penten-1-amine, (4E) and (4Z)-N-methyl-5-(3-pyridyl)-4-methyl-4-penten-2-amine, (1E) and (1Z)-N-methyl-1-(3-pyridyl)-1-octen-4-amine, (1E) and (1Z)-N-methyl-1-(3-pyridyl)-5-methyl-1-hepten-4-amine, (5E) and (5Z)-N-methyl-6-(3-pyridyl)-5-methyl-5-hexen-2-amine, (5E) and (5Z)-N-methyl-6-(3-pyridyl)-5-hexen-2-amine, (5E) and (5Z)-N-methyl-6-(3-pyridyl)-5-methyl-5-hexen-3-amine, (3E) and (3Z)-4-(3-pyridyl)-2-methyl-3-buten-1-amine, (3E) and (3Z)-4-(3-pyridyl)-3-methyl-3-buten-1-amine, (5E) and (5Z)-6-(3-pyridyl)-5-hexen-3-amine, (4E) and (4Z)-5-(3-pyridyl)-2-methyl-4-penten-2-amine, (4E) and (4Z)-5-(3-pyridyl)-3-methyl-4-penten-2-amine, (4E) and (4Z)-5-(3-pyridyl)-4-penten-2-amine, (4E) and (4Z)-5-(3-pyridyl)-1,1,1-trifluoro-4-penten-2-amine, (4E) and (4Z)-5-(3-pyridyl)-4-methyl-4-penten-1-amine, (4E) and (4Z)-5-(3-pyridyl)-4-methyl-4-penten-2-amine, (1E) and (1Z)-1-(3-pyridyl)-1-octen-4-amine, (5E) and (5Z)-6-(3-pyridyl)-5-methyl-5-hexen-2-amine, (5E) and (5Z)-6-(3-pyridyl)-5-hexen-2-amine, and (5E) and (5Z)-6-(3-pyridyl)-5-methyl-5-hexen-3-amine. See, U.S. Pat. No. 5,616,716 to Dull et al.

The manner in which aryl substituted olefinic amine compounds of the present invention are synthetically produced can vary. (E)-metanicotine-type compounds can be prepared using the techniques set forth by Löffler et al., Chem. Ber., 42, pp. 3431–3438 (1909) and Laforge, J.A.C.S., 50, p. 2477 (1928) from substituted nicotine-type compounds. Certain 6-substituted metanicotine-type compounds can be prepared from the corresponding 6-substituted nicotine-type compounds using the general methods of Acheson et al., J. Chem. Soc., Perkin Trans. 1, 2, pp. 579–585 (1980). The requisite precursors for such compounds, 6-substituted nicotine-type compounds, can be synthesized from 6-substituted nicotinic acid esters using the general methods disclosed by Rondahl, Acta Pharm. Suec., 14, pp 113–118 (1977). Preparation of certain 5-substituted metanicotine-type compounds can be accomplished from the corresponding 5-substituted nicotine-type compounds using the general method taught by Acheson et al., J. Chem. Soc., Perkin Trans. 1, 2, pp. 579–585 (1980). The 5-halo-substituted nicotine-type compounds (e.g., fluoro- and bromo-substituted nicotine-type compounds) and the 5-amino nicotine-type compounds can be prepared using the general procedures disclosed by Rondahl, Act. Pharm. Suec., 14, pp. 113–118 (1977). The 5-trifluoromethyl nicotine-type compounds can be prepared using the techniques and materials set forth in Ashimori et al., Chem. Pharm. Bull., 38(9), pp. 2446–2458 (1990) and Rondahl, Acta Pharm. Suec., 14, pp.113–118 (1977).

Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo-substituted, 5-substituted pyridine compound or a 5-halo-substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., J. Org. Chem., 43(15), pp. 2947–2949 (1978) and Malek et al., J. Org. Chem., 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group then affords the desired metanicotine-type compound.

There are a number of different methods for providing (Z)-metanicotine-type compounds. In one method, (Z)-metanicotine-type compounds can be synthesized from nicotine-type compounds as a mixture of E and Z isomers; and the (Z)-metanicotine-type compounds can then be separated by chromatography using the types of techniques disclosed by Sprouse et al., Abstracts of Papers, p. 32, Coresta/TCRC Joint Conference (1972). In another method, metanicotine-type compounds can be prepared by the controlled hydrogenation of the corresponding acetylenic compound (e.g., an N-methyl-4-(3-pyridinyl)-3-butyn-1-amine type compound). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively. Representative synthetic techniques for (Z)-metanicotine-type compounds are set forth in U.S. Pat. No. 5,597,919 to Dull et al.

There are a number of methods by which the (Z)-olefinic isomers of aryl substituted olefinic amine compounds can be synthetically produced. In one approach, the (Z)-isomers of aryl substituted olefinic amine compounds can be prepared by the controlled hydrogenation of the corresponding alkynyl compounds (e.g., a N-methyl-5-(3-pyridyl)-4-butyn-2-amine-type compound) using commercially available Lindlar catalyst (Aldrich Chemical Company) using the methodology set forth in H. Lindlar et al., Org. Syn. 46: 89 (1966). The requisite alkynyl compounds can be prepared by the palladium catalyzed coupling of an aromatic halide, preferably a 3-bromopyridine-type or a 3-iodopyridine-type compound with an alkynyl side chain compound (e.g., an N-methyl-4-pentyn-2-amine-type compound). Typically the methodology set forth in L. Bleicher et al., *Synlett.* 1115 (1995) is used for the palladium catalyzed coupling of an aryl halide with a monosubstituted alkyne in the presence of copper(I) iodide and triphenylphosphine and potassium carbonate as a base. Alkynyl compounds such as N-methyl-4-pentyn-2-amine can be prepared from commercially available 4-pentyn-2-ol (Aldrich Chemical Company) by treatment with p-toluenesulfonyl chloride in pyridine, followed by reaction of the resulting 4-pentyn-2-ol p-toluenesulfonate with excess methylamine either as a 40% aqueous solution or as a 2.0 M solution in tetrahydrofuran. In some instances it may be necessary to protect the amino functionality of the N-methyl-4-pentyn-2-amine-type compound by treatment with di-tert-butyl dicarbonate to give the tert-butoxycarbonyl protected amine-type compound. Such protected amine compounds may undergo the palladium catalyzed coupling with aryl halides and the subsequent controlled hydrogenation of the resulting alkynyl compound more easily than the unprotected amine compounds. The tert-butoxycarbonyl protecting group can be easily removed using a strong acid such as trifluoroacetic acid to yield the (Z)-olefinic isomers of aryl substituted olefinic amine compounds.

The methods by which aryl substituted olefinic amine compounds of the present invention can be synthetically produced can vary. An olefinic alcohol, such as 4-penten-2-ol, is condensed with an aromatic halide, such as 3-bromopyridine or 3-iodopyridine. Typically, the types of procedures set forth in Frank et al., *J. Org. Chem.,* 43, pp. 2947–2949 (1978) and Malek et al., *J. Org. Chem.,* 47, pp. 5395–5397 (1982) involving a palladium-catalyzed coupling of an olefin and an aromatic halide are used. The olefinic alcohol optionally can be protected as a t-butyldimethylsilyl ether prior to the coupling. Desilylation then produces the olefinic alcohol. The alcohol condensation product then is converted to an amine using the type of procedures set forth in deCosta et al., *J. Org. Chem.,* 35, pp. 4334–4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-1-hepten-4-ol, 4-methyl-5-hexen-2-ol, 5-methyl-5-hexen-2-ol, 5-hexen-2-ol and 5-methyl-5-hexen-3-ol. Trifluoromethyl-substituted olefinic alcohols, such as 1,1,1-trifluoro-4-penten-2-ol, can be prepared from 1-ethoxy-2,2,2-trifluoroethanol and allyltrimethylsilane using the procedures of Kubota et al., *Tetrahedron Letters, Vol.* 33(10), pp. 1351–1354 (1992), or from trifluoroacetic acid ethyl ester and allyltributylstannane using the procedures of Ishihara et al., *Tetrahedron Letters, Vol.* 34(56), pp. 5777–5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Preferred aromatic halides are 3-bromopyridine-type compounds and 3-iodopyridine-type compounds. Typically, substituent groups of such 3-halopyridine-type compounds are such that those groups can survive contact with those chemicals (e.g., tosylchloride and methylamine) and the reaction conditions experienced during the preparation of the aryl substituted olefinic amine compound. Alternatively, substituents such as —OH, —$NH_2$ and —SH can be protected as corresponding acyl compounds, or substituents such as —$NH_2$ can be protected as a phthalimide functionality.

The manner in which certain aryl substituted olefinic amine compounds possessing a branched side chain, such as (4E)-N-methyl-5-(5-isopropoxy-3-pyridyl)-4-penten-2-amine, are provided can vary. By using one synthetic approach, the latter compound can be synthesized in a convergent manner, in which the side chain, N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required N-methyl-N-(tert-butoxycarbonyl)-4-penten-2-amine can be synthesized as follows: (i) Commercially available 4-penten-2-ol (Aldrich Chemical Company, Lancaster Synthesis Inc.) can be treated with p-toluenesulfonyl chloride in pyridine to yield 4-penten-2-ol p-toluenesulfonate, previously described by T. Michel, et al., *Liebigs Ann.* 11: 1811 (1996). (ii) The resulting tosylate can be heated with 20 molar equivalents of methylamine as a 40% aqueous solution to yield N-methyl-4-penten-2-amine. (iii) The resulting amine, such as previously mentioned by A. Viola et al., *J. Chem. Soc., Chem. Commun.* (21): 1429 (1984), can be allowed to react with 1.2 molar equivalents of di-tert-butyl dicarbonate in dry tetrahydrofuran to yield the side chain, N-methyl-N-(tert-butoxycarbonyl)-4-penten-2-amine. The halo-substituted pyridine, (e.g., 5-bromo-3-isopropoxypyridine) can be synthesized by two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia. (ii) The resulting 5-bromonicotinamide, previously described by C. V. Greco et al., *J. Heteocyclic Chem.* 7(4): 761 (1970), is subjected to Hofmann degradation by treatment with sodium hydroxide and a 70% solution of calcium hypochlorite. (iii) The resulting 3-amino-5-bromopyridine, previously described by C. V. Greco et al., *J. Heteocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and N-methyl-N-(tert-butoxycarbonyl)-4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (4E)-N-methyl-N-(tert-butoxycarbonyl)-5-(5-isopropoxy-3-pyridyl)-4-penten-2-amine. Removal of the tert-butoxycarbonyl protecting group can be accomplished by treatment with 30 molar equivalents of trifluoroacetic acid in anisole at 0° C. to afford (4E)-N-methyl-5-(5-isopropoxy-3-pyridyl)-4-penten-2-amine.

The manner in which certain aryl substituted olefinic amine compounds possessing a branched side chain are provided can vary. Using one synthetic approach, a compound such as (4E)-N-methyl-5-(5-methoxy-3-pyridyl)-4-penten-2-amine can be synthesized by coupling a halo-substituted pyridine, 5-bromo-3-methoxypyridine with an olefin containing a secondary alcohol functionality, 4-penten-2-ol, under Heck reaction conditions; and the resulting pyridyl alcohol intermediate can be converted to its p-toluenesulfonate ester, followed by treatment with methylamine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required halo-substituted pyridine, 5-bromo-3-methoxypyridine is synthesized using methodology similar to that described by H. J. den Hertog et al., *Recl. Trav. Chim. Pays-Bas* 74:1171 (1955), namely by heating 3,5-dibromopyridine with 2.5 molar equivalents of sodium methoxide in dry methanol in the presence of copper powder (5%, w/w of the 3,5-dibromopyridine) in a sealed glass tube at 150° C. for 14 hours to produce 5-bromo-3-methoxypyridine. The resulting 5-bromo-3-methoxypyridine, previously described by D. L. Comins, et al., *J. Org. Chem.* 55: 69 (1990), can be coupled with 4-penten-2-ol in acetonitrile-triethylamine (1.1:1, v/v) using a catalyst consisting of 1 mole % palladium(II) acetate and 4 mole % tri-o-tolylphosphine. The reaction is carried out by heating the components in a sealed glass tube at 140° C. for 14 hours to yield (4E)-N-methyl-5-(5-methoxy-3-pyridyl)-4-penten-2-ol. The resulting alcohol is treated with 2 molar equivalents of p-toluenesulfonyl chloride in dry pyridine at 0° C. to produce (4E)-N-methyl-5-(5-methoxy-3-pyridyl)-4-penten-2-ol p-toluensulfonate. The tosylate intermediate is treated with 120-molar equivalents of methylamine as a 40% aqueous solution, containing a small amount of ethanol as a co-solvent to produce (4E)-N-methyl-5-(5-methoxy-3-pyridyl)-4-penten-2-amine.

The manner in which optically active forms of certain aryl substituted olefinic amine compounds, such as (2S)-(4E)-N-methyl-5-(3-pyridyl)-4-penten-2-amine, are provided can vary. In one synthetic approach, the latter type of compound is synthesized by coupling a halo-substituted pyridine, 3-bromopyridine, with an olefin possessing a chiral, secondary alcohol functionality, (2R)-4-penten-2-ol, under Heck reaction conditions. The resulting chiral pyridyl alcohol intermediate, (2R)-(4E)-5-(3-pyridyl)-4-penten-2-ol is converted to its corresponding p-toluenesulfonate ester, which is subsequently treated with methylamine, resulting in tosylate displacement with inversion of configuration. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide in tetrahydrofuran at low temperatures (−25 to −10° C.) using the general synthetic methodology of A. Kalivretenos, J. K. Stille, and L. S. Hegedus, *J. Org. Chem.* 56: 2883 (1991), to afford (2R)-4-penten-2-ol. The resulting chiral alcohol is subjected to a Heck reaction with 3-bromopyridine in acetonitrile-triethylamine (1:1, v/v) using a catalyst consisting of 1 mole % palladium(II) acetate and 4 mole % tri-o-tolylphosphine. The reaction is done by heating the components at 140° C. for 14 hours in a sealed glass tube, to produce the Heck reaction product, (2R)-(4E)-5-(3-pyridyl)-4-penten-2-ol. The resulting chiral pyridyl alcohol is treated with 3 molar equivalents of p-toluenesulfonyl chloride in dry pyridine at 0° C., to afford the tosylate intermediate. The p-toluenesulfonate ester is heated with 82 molar equivalents of methylamine as a 40% aqueous solution, containing a small amount of ethanol as a co-solvent, to produce (2S)-(4E)-N-methyl-5-(3-pyridyl)-4-penten-2-amine.

In a similar manner, the corresponding aryl substituted olefinic amine enantiomer, such as (2R)-(4E)-N-methyl-5-(3-pyridyl)-4-penten-2-amine, can be synthesized by the Heck coupling of 3-bromopyridine and (2S)-4-penten-2-ol. The resulting intermediate, (2S)-(4E)-5-(3-pyridyl)-4-penten-2-ol, is converted to its p-toluenesulfonate, which is subjected to methylamine displacement. The chiral alcohol, (2S)-4-penten-2-ol, is prepared from (S)-(−)-propylene oxide (commercially available from Aldrich Chemical Company) using a procedure analogous to that described for the preparation of (2R)-4-penten-2-ol from (R)-(+)-propylene oxide as reported by A. Kalivretenos, J. K. Stille, and L. S. Hegedus, *J. Org. Chem.* 56: 2883 (1991).

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae which are set forth hereinbefore. The present invention relates to a pharmaceutical composition incorporating a compound selected from the general formulae which are set forth hereinbefore. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. Nos. 5,597,919 to Dull et al., 5,616,716 to Dull et al. and 5,663,356 to Ruecroft et al.

Compounds of the present invention are useful for treating those types of conditions and disorders for which other types of nicotinic compounds have been proposed as therapeutics. See, for example, Williams et al. *DN&P* 7(4): 205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. Nos. 5,583,140 to Bencherif et al., 5,597,919 to Dull et al., and 5,604,231 to Smith et al. Compounds of the present invention can be used as analgesics, to treat ulcerative colitis, and to treat convulsions such as those that are symptomatic of epilepsy. CNS disorders which can be treated in accordance with the present invention include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that affect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. No. 5,604,231 to Smith et al., the disclosure of which is incorporated herein by reference in its entirety.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder. Relative to (E)-metanicotine, compounds of the present invention are less extensively metabolized (i.e., fewer metabolites are formed, and the rate of elimination from blood is slower) in mammalian systems. As such, as compared to (E)-metanicotine, compounds of the present invention are capable of providing higher absolute plasma concentrations, and are capable of being maintained within a mammalian system for longer periods of time. Thus, compounds of the present invention are capable of providing comparable therapeutic effects of (E)-metanicotine at low doses.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 5 mg/kg of patient weight. Often, the compounds of the present invention are administered in an amount from 1 mg to less than 100 $\mu$g/kg of patient weight, frequently between about 10 $\mu$g to less than 100 $\mu$g/kg of patient weight, and preferably between about 10 $\mu$g to about 50 $\mu$g/kg of patient weight. For compounds of the present invention that do not induce effects on muscle type nicotinic receptors at low concentrations, the effective dose is less than 5 mg/kg of patient weight; and often such compounds are administered in an amount from 50 μg to less than 5 mg/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 μg/24 hr./patient. For human patients, the effective dose of typical compounds requires administering the compound which generally does not exceed about 500, often does not exceed about 400, and frequently does not exceed about 300 μg/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1. The log P values of such typical compounds generally are less than about 3.5, often are less than about 3, and sometimes are less than about 2.5. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause activation of, nicotinic cholinergic receptors of the brain of the patient (e.g., such as those receptors that modulate dopamine release). As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 μM often are less than about 100 nM, and frequently are less than about 50 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively eliciting ion flux through, and/or neurotransmitter secretion from, nerve ending preparations (e.g., thalamic or striatal synaptosomes). As such, such compounds have the ability to cause relevant neurons to become activated, and to release or secrete acetylcholine, dopamine, or other neurotransmitters. Generally, typical compounds useful in carrying out the present invention effectively provide for relevant receptor activation in amounts of at least about 30 percent, often at least about 50 percent, and frequently at least about 75 percent, of that maximally provided by (S)-(−)-nicotine. Generally, typical compounds useful in carrying out the present invention are more potent than (S)-(−)-nicotine in eliciting relevant receptor activation. Generally, typical compounds useful in carrying out the present invention effectively provide for the secretion of dopamine in amounts of at least about 50 percent, often at least about 75 percent, and frequently at least about 100 percent, of that maximally provided by (S)-(−)-nicotine. Certain compounds of the present invention can provide secretion of dopamine in an amount which can exceed that maximally provided by (S)-(−)-nicotine. Generally, typical compounds useful in carrying out the present invention are less potent than (S)-(−)-nicotine in eliciting neurotransmitter secretion, such as dopamine secretion.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations expressing muscle-type nicotinic acetylcholine receptors. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 100 μM). Generally, typical preferred compounds useful in carrying the present invention activate isotopic rubidium ion flux by less than 10 percent, often by less than 5 percent, of that maximally provided by S(−) nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical preferred compounds useful in carrying out the present invention activate isotopic rubidium ion flux by less than 10 percent, often by less than 5 percent, of that maximally provided by S(−) nicotine.

Compounds of the present invention, when employed in effective amounts in accordance with the method of the present invention, are effective towards providing some degree of prevention of the progression of CNS disorders, amelioration of the symptoms of CNS disorders, and amelioration to some degree of the recurrence of CNS disorders. However, such effective amounts of those compounds are not sufficient to elicit any appreciable side effects, as is demonstrated by decreased effects on preparations believed to reflect effects on the cardiovascular system, or effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less ⅓, frequently less than ⅕, and often less than 1/10, that amount sufficient to cause any side effects to a significant degree.

The following examples are provided to illustrate the present invention, and should not be construed as limiting thereof. In these examples, all parts and percentages are by weight, unless otherwise noted. Reaction yields are reported in mole percentages. Several commercially available starting materials are used throughout the following examples. 3-Bromopyridine, 3,5-dibromopyridine, 5-bromonicotinic acid, 5-bromopyrimidine, and 4-penten-2-ol were obtained from Aldrich Chemical Company or Lancaster Synthesis Inc. 2-Amino-5-bromo-3-methylpyridine was purchased from Maybridge Chemical Company Ltd. (R)-(+)-propylene oxide was obtained from Fluka Chemical Company, and (S)-(−)-propylene oxide was obtained from Aldrich Chemical Company. Column chromatography was done using either Merck silica gel 60 (70–230 mesh) or aluminum oxide (activated, neutral, Brockmann I, standard grade, ~150 mesh). Pressure reactions were done in a heavy wall glass pressure tube (185 mL capacity), with Ace-Thread, and plunger valve available from Ace Glass Inc. Reaction mixtures were typically heated using a high-temperature silicon oil bath, and temperatures refer to those of the oil bath. The following abbreviations are used in the following examples: $CHCl_3$ for chloroform, $CH_2Cl_2$ for dichloromethane, $CH_3OH$ for methanol, DMF for N,N-dimethylformamide, and EtOAc for ethyl acetate, THF for tetrahydrofuran, and $Et_3N$ for triethylamine.

EXAMPLE 1

Determination of Log P Value

Log P values, which have been used to assess the relative abilities of compounds to pass across the blood-brain barrier (Hansch, et al., *J. Med. Chem.* ii:1(1968)), were calculated using the Cerius$^2$ software package Version 3.5 by Molecular Simulations, Inc.

EXAMPLE 2

Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., *Biochem, Pharmacol.* 22:3099 (1973).

EXAMPLE 3

Determination of Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported $EC_{50}$ values are expressed in nM, and $E_{max}$ values represent the amount released relative to (S)-(−)-nicotine on a percentage basis.

EXAMPLE 4

Determination of Rubidium Ion Release

Rubidium release was measured using the techniques described in Bencherif et al., *JPET,* 279: 1413–1421 (1996). Reported $EC_{50}$ values are expressed in nM, and $E_{max}$ values represent the amount of rubidium ion released relative to 300 $\mu$M tetramethylammonium ion, on a percentage basis.

EXAMPLE 5

Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

EXAMPLE 6

Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

EXAMPLE 7

Sample No. 1 is (4E)-N-methyl-5-(3-pyridyl)-4-penten-2-amine hemigalactarate, which was prepared in accordance with the following techniques:

(4E)-5-(3-Pyridyl)-4-penten-2-ol

A mixture of 3-bromopyridine (7.50 g, 47.46 mmol), 4-penten-2-ol (4.90 g, 56.96 mmol), palladium(II) acetate (106 mg, 0.47 mmol), tri-o-tolylphosphine (575 mg, 1.89 mmol), triethylamine (28.4 mL, 204.11 mmol) and acetonitrile (25 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate, filtered, and concentrated by rotary evaporation to give a pale-yellow oil (7.50 g, 81.0%).

(4E)-5-(3-Pyridyl)-4-penten-2-ol p-Toluenesulfonate

To a stirred solution of (4E)-5-(3-pyridyl)-4-penten-2-ol (5.00 g, 30.67 mmol) in dry pyridine (30 mL) at 0° C. was added p-toluenesulfonyl chloride (8.77 g, 46.01 mmol). The reaction mixture was stirred for 24 h at ambient temperature. The pyridine was removed by rotary evaporation. Toluene (50 mL) was added to the residue and subsequently removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-hexane (3:7, v/v). Selected fractions were combined and concentrated by rotary evaporation to give a viscous, brown oil (5.83 g, 60.1%).

(4E)-N-Methyl-5-(3-pyridyl)-4-penten-2-amine

A mixture of (4E)-5-(3-pyridyl)-4-penten-2-ol p-toluenesulfonate (5.60 g, 17.66 mmol), methylamine (100 mL, 40% solution in water), and ethyl alcohol (10 mL) was stirred at ambient temperature for 18 h. The resulting solution was extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-methanol (7:3, v/v). Selected fractions were combined and concentrated by rotary evaporation, producing an oil. Further purification by vacuum distillation furnished 1.60 g (51.6%) of a colorless oil, bp 110–120° C. at 0.1 mm Hg.

(4E)-N-Methyl-5-(3-pyridyl)-4-penten-2-amine Hemigalactarate (4E)-N-Methyl-5-(3-pyridyl)-4-penten-2-amine (1.60 g, 9.10 mmol) was dissolved in ethyl alcohol (20 mL), assisted by warming to 60° C. The warm solution was treated with galactaric acid (955 mg, 4.54 mmol) in one portion, followed by the dropwise addition of water (0.5 mL). The solution was filtered while hot to remove some insoluble material. The filtrate was allowed to cool to ambient temperature. The resulting crystals were filtered, washed with anhydrous diethyl ether, and dried under vacuum at 40° C. to yield 1.20 g (47.0%) of a white, crystalline powder, mp 148–150° C.

Sample No. 1 exhibits a log P of 1.924, and such a favorable log P value indicates that the compound has the capability of passing the blood-brain barrier. The sample exhibits a Ki of 83 nM. The low binding constant indicates that the compound exhibits good high affinity binding to certain CNS nicotinic receptors.

Sample No. 1 exhibits an $EC_{50}$ value of 6600 nM and an $E_{max}$ value of 113% for dopamine release, indicating that the compound induces neurotransmitter release thereby exhibiting known nicotinic pharmacology. The sample exhibits an $EC_{50}$ value of 3100 nM and an $E_{max}$ value of 35% in the rubidium ion flux assay, indicating that the compound effectively induces activation of CNS nicotinic receptors.

Sample No. 1 exhibits an $E_{max}$ of 13% (at a concentration of 100 M) at muscle-type receptors, indicating that the compound does not induce activation of muscle-type receptors. The sample exhibits an $E_{max}$ of 62% (at a concentration of 100 $\mu$M) at ganglionic-type receptors. At certain levels the compound shows CNS effects to a significant degree but show neither undesirable muscle nor ganglion effects to any significant degree. The compound begins to cause muscle and ganglion effects only when employed in amounts of several times those required to activate rubidium ion flux and dopamine release, thus indicating a lack of certain undesirable side effects in subjects receiving administration of that compound.

EXAMPLE 8

Sample No. 2 is (2R)-(4E)-N-methyl-5-(3-pyridyl)-4-penten-2-amine hemigalactarate, which was prepared in accordance with the following techniques:

(2S)-4-Penten-2-ol (2S)-4-Penten-2-ol was prepared from (S)-(−)-propylene oxide using a procedure similar to that described for the preparation of (2R)-4-penten-2-ol from (R)-(+)-propylene oxide as detailed in A. Kalivretenos, J. K. Stille, and L. S. Hegedus, *J. Org. Chem.* 56: 2883 (1991). Thus, a 1.0M solution of vinylmagnesium bromide in THF (129 mL, 129.0 mmol) was slowly added to a suspension of copper(I) iodide (2.46 g, 12.92 mmol) in dry THF (40 mL, distilled from sodium and benzophenone) at −25° C. After stirring 5 min, a solution of (S)-(−)-propylene oxide (5.00 g, 86.1 mmol) in dry THF (5 mL) was added. The mixture was allowed to warm to −10° C. and placed in a freezer at 0° C. for 12 h. The mixture was stirred for an additional 1 h at 0° C. and poured into a mixture of saturated ammonium chloride solution (100 mL) and ice (100 g). The mixture was stirred for 4 h and extracted with ether (3×100 mL). The combined ether extracts were dried ($K_2CO_3$), filtered, and concentrated under reduced pressure by rotary evaporation at 0° C. The resulting brown oil was vacuum distilled to yield 5.86 g (79.1%) of a colorless distillate, bp 37–39° C. at 9 mm Hg.

(2S)-(4E)-5-(3-Pyridyl)-4-penten-2-ol

A mixture of 3-bromopyridine (11.22 g, 70.58 mmol), (2S)-4-penten-2-ol (5.00 g, 58.05 mmol), palladium(II) acetate (527 mg, 2.35 mmol), tri-o-tolylphosphine (1.79 g, 5.88 mmol), triethylamine (30 mL, 216 mmol) and acetonitrile (30 mL) were heated in a sealed glass tube at 130–140° C. for 8 h. The reaction mixture was cooled to ambient temperature. The solvent was removed under reduced pressure on a rotary evaporator. Water (20 mL) was added and the mixture was extracted with chloroform (4×50 mL). The combined chloroform extracts were dried ($K_2CO_3$), filtered, and concentrated by rotary evaporation, producing a pale-yellow oil (6.00 g). The crude product was purified by column chromatography over silica gel, eluting with chloroform-acetone (95:5, v/v). Selected fractions were combined and concentrated by rotary evaporation, affording 3.95 g (41.7%) of a pale-yellow oil.

(2S)-(4E)-5-(3-Pyridyl)-4-penten-2-ol p-Toluenesufonate

Under a nitrogen atmosphere, p-toluenesufonyl chloride (7.01 g, 36.77 mmol) was added to a stirring solution of (2S)-(4E)-5-(3-pyridyl)-4-penten-2-ol (3.00 g, 18.38 mmol) in dry triethylamine (20 mL) at 0° C. After stirring and warming to ambient temperature over 18 h, the mixture was stirred with cold, saturated $NaHCO_3$ solution (50 mL) for 1 hour and extracted with chloroform (3×50 mL). The combined chloroform extracts were dried ($K_2CO_3$), filtered, and concentrated by rotary evaporation to afford a thick, dark-brown mass (~7 g). The crude product was purified by column chromatography on silica gel, eluting with chloroform-acetone (98:2, v/v) to afford 4.00 g (68.6%) of a light-brown syrup.

(2R)-(4E)-N-Methyl-5-(3-pyridyl)-4-penten-2-amine

A mixture of (2S)-(4E)-5-(3-pyridyl)-4-penten-2-ol p-toluenesulfonate (3.80 g, 11.97 mmol) and methylamine (20 mL, 2.0M solution in THF) was heated at 100–110° C. for 8 h in a sealed glass tube. The mixture was cooled to ambient temperature and concentrated under reduced pressure on a rotary evaporator. The resulting brown syrup was diluted with saturated $NaHCO_3$ solution (25 mL) and extracted with chloroform (4×25 mL). The combined chloroform extracts were dried ($K_2CO_3$), filtered, and concentrated by rotary evaporation to afford a thick, brown syrup (2.00 g). The crude product was purified by column chromatography on silica gel, eluting with chloroform-methanol (95:5, v/v). Selected fractions were combined, concentrated by rotary evaporation affording a 800 mg (37.9%) of a pale-yellow oil.

(2R)-(4E)-N-Methyl-5-(3-pyridyl)-4-penten-2-amine Hemigalactarate

Galactaric acid (328.0 mg, 1.56 mmol) and (2R)-(4E)-N-methyl-5-(3-pyridyl)-4-penten-2-amine (600.0 mg, 3.40 mmol) were dissolved in 2-propanol (5 mL) and water (0.2 mL), assisted by heating and sonication. The hot solution was filtered to remove some insoluble material. The solvent was removed on a rotary evaporator, and the residue was dried under high vacuum, producing a cream-colored syrup. The syrup was dissolved in dry 2-propanol (5 mL) and cooled at 4° C. The resulting precipitate was filtered and dried under high vacuum to yield 700 mg (79.7%) of an off-white, crystalline powder, mp 131–134° C.

Sample No. 2 exhibits a log P of 1.924, and such a favorable log P value indicates that the compound has the capability of passing the blood-brain barrier. The sample exhibits a Ki of 520 nM, indicating that the compound exhibits binding to certain CNS nicotinic receptors.

Sample No. 2 exhibits an $EC_{50}$ value of 27400 nM and an $E_{max}$ value of 76% for dopamine release, indicating that the compound induces neurotransmitter release thereby exhibiting known nicotinic pharmacology. The sample exhibits an $EC_{50}$ value of 4390 nM and an $E_{max}$ value of 32% in the rubidium ion flux assay, indicating that the compound induces activation of CNS nicotinic receptors.

Sample No. 2 exhibits an $E_{max}$ of 0% (at a concentration of 100 μM) at muscle-type receptors, indicating that the compound does not induce activation of muscle-type receptors. Sample No. 1 exhibits an $E_{max}$ of 36% (at a concentration of 100 μM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglion effects to any significant degree.

EXAMPLE 9

Sample No. 3 (2S)-(4E)-N-methyl-5-(3-pyridyl)-4-penten-2-amine hemigalactarate, which was prepared in accordance with the following techniques:

(2R)-4-Penten-2-ol (2R)-4-Penten-2-ol was prepared in 82.5% yield from (R)-(+)-propylene oxide according to procedures set forth in A. Kalivretenos, J. K. Stille, and L. S. Hegedus, *J. Org. Chem.* 56: 2883 (1991).

(2R)-(4E)-5-(3-Pyridyl)-4-penten-2-ol

A mixture of 3-bromopyridine (9.17 g, 58.04 mmol), (2R)-4-penten-2-ol (6.00 g, 69.65 mmol), palladium(II) acetate (130 mg, 0.58 mmol), tri-o-tolylphosphine (710 mg, 2.32 mmol), triethylamine (34.7 mL, 249.5 mmol), and acetonitrile (35 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate, filtered, and concentrated by rotary evaporation to give 6.17 g (65.2%) of a pale-yellow oil.

(2R)-(4E)-5-(3-Pyridyl)4-penten-2-ol p-Toluenesulfonate

To a stirring solution of (2R)-(4E)-5-(3-pyridyl)-4-penten-2-ol (6.00 g, 36.81 mmol) in dry pyridine (30 mL) at 0° C. was added p-toluenesulfonyl chloride (21.05 g, 110.43 mmol). The reaction mixture was stirred for 24 h at ambient temperature. The pyridine was removed by rotary evaporation. Toluene (50 mL) was added to the residue and subsequently removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation to give 11.67 g (84.0%) of a dark-brown, viscous oil.

(2S)-(4E)-N-Methyl-5-(3-pyridyl)-4-penten-2-amine

A mixture of (2R)-(4E)-5-(3-pyridyl)-4-penten-2-ol p-toluenesulfonate (9.00 g, 28.35 mmol), methylamine (200 mL, 40% solution in water), and ethyl alcohol (10 mL) was stirred at ambient temperature for 18 h. The resulting solution was extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-methanol (7:3, v/v). Selected fractions were combined and concentrated by rotary evaporation, producing an oil. Further purification by vacuum distillation furnished 1.20 g (24.0%) of a colorless oil, bp 90–100° C. at 0.5 mm Hg.

(2S)-(4E)-N-Methyl-5-(3-pyridyl)-4-penten-2-amine Hemigalactarate (2S)-(4E)-N-Methyl-5-(3-pyridyl)-4-penten-2-amine (800 mg, 4.54 mmol) was dissolved in ethyl alcohol (20 mL), assisted by warming to 60° C. The warm solution was treated with galactaric acid (477 mg, 2.27 mmol) in one portion, followed by the dropwise addition of water (0.5 mL). The solution was filtered while hot to remove some insoluble material. The filtrate was allowed to cool to ambient temperature. The resulting crystals were filtered, washed with anhydrous diethyl ether, and dried under vacuum at 40° C. to yield 830 mg (65.4%) of an off-white, crystalline powder, mp 141–143° C.

Sample No. 3 exhibits a log P of 1.924, and such a favorable log P value indicates that the compound has the capability of passing the blood-brain barrier. The sample exhibits a Ki of 34 nM. The low binding constant indicates that the compound exhibits good high affinity binding to certain CNS nicotinic receptors.

Sample No. 3 exhibits an $EC_{50}$ value of 2600 nM and an $E_{max}$ value of 162% for dopamine release, indicating that the compound effectively induces neurotransmitter release thereby exhibiting known nicotinic pharmacology. The sample exhibits an $EC_{50}$ value of 45 nM and an $E_{max}$ value of 33% in the rubidium ion flux assay, indicating that the compound effectively induces activation of CNS nicotinic receptors.

Sample No. 3 exhibits an $E_{max}$ of 0% (at a concentration of 100 μM) at muscle-type receptors, indicating that the compound does not induce activation of muscle-type receptors. The sample exhibits an $E_{max}$ of 18% (at a concentration of 100 μM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle or ganglion effects to any significant degree.

EXAMPLE 10

Sample No. 4 is (4E)-N-methyl-5-(5-isopropoxy-3-pyridyl)-4-penten-2-amine hemigalactarate, which was prepared in accordance with the following techniques:

4-Penten-2-ol p-Toluenesulfonate

Under a nitrogen atmosphere, p-toluenesulfonyl chloride (16.92 g, 88.75 mmol) was added to a cold (2° C.), stirring solution of 4-penten-2-ol (7.28 g, 84.52 mmol) in pyridine (60 mL). The solution was stirred at 2–5° C. for 2 h and allowed to warm to ambient temperature over several hours. The mixture, containing white solids, was poured into cold 3M HCl solution (250 mL) and extracted with $CHCl_3$ (4×75 mL). The combined $CHCl_3$ extracts were washed with 3M HCl solution (4×100 mL), saturated NaCl solution (2×50 mL), dried ($Na_2SO_4$), filtered, concentrated on a rotary evaporator, and further dried under high vacuum to afford 17.38 g (85.6%) of a light-amber oil.

N-Methyl-4-penten-2-amine

A glass pressure tube was charged with 4-penten-2-ol p-toluenesulfonate (17.30 g, 71.99 mmol) followed by a 40% solution of aqueous methylamine (111.85 g, 1.44 mol). The tube was sealed, and the mixture was stirred and heated at 122° C. for 16 h and allowed to cool to ambient temperature. After further cooling to 0–5° C., the light-yellow solution was saturated with solid NaCl and extracted with diethyl ether (6×40 mL, inhibitor-free). The combined light-yellow ether extracts were dried ($Na_2SO_4$) and filtered. The ether was removed by distillation at atmospheric pressure using a 6-inch Vigreaux column and a short-path distillation apparatus. The residual light-yellow oil was distilled at atmospheric pressure collecting 3.72 g (52.1%) of a colorless oil, bp 75–105° C.

N-Methyl-N-(tert-butoxycarbonyl)-4-penten-2-amine

Di-tert-butyl dicarbonate (6.84 g, 31.35 mmol) was quickly added in several portions to a cold (0–5° C.), stirring solution of N-methyl-4-penten-2-amine (3.66 g, 25.68 mmol) in dry THF (25 mL, freshly distilled from sodium and benzophenone). The resulting light-yellow solution was stirred and allowed to warm to ambient temperature over several hours. The solution was concentrated on a rotary evaporator. The resulting oil was vacuum distilled using a short-path distillation apparatus, collecting 5.22 g (88.4%) of an almost colorless oil, bp 85–86° C. at 5.5 mm Hg.

5-Bromo-3-isopropoxypyridine can be prepared by two different methods (Method A and Method B) as described below.

5-Bromo-3-isopropoxypyridine (Method A)

Potassium metal (6.59 g, 168.84 mmol) was dissolved in dry 2-propanol (60.0 mL) under nitrogen. The resulting potassium isopropoxide was heated with 3,5-dibromopyridine (20.00 g, 84.42 mmol) and copper powder (1 g, 5% by weight of 3,5-dibromopyridine) at 140° C. in a sealed glass tube for 14 h. The reaction mixture was cooled to ambient temperature and extracted with diethyl ether (4×200 mL). The combined ether extracts were dried over sodium sulfate, filtered, and concentrated by rotary evaporation. The crude product obtained was purified by column chromatography over aluminum oxide, eluting with ethyl acetate-hexane (1:9, v/v). Selected fractions were combined and concentrated by rotary evaporation, producing a pale-yellow oil (12.99 g, 71.2%).

5-Bromo-3-isopropoxypyridine (Method B)

5-Bromonicotinamide

Under a nitrogen atmosphere, 5-bromonicotinic acid (10.10 g, 50.00 mmol) was dissolved in thionyl chloride (65.24 g, 0.55 mol), and the resulting solution was stirred 45 min at ambient temperature. Excess thionyl chloride was removed by distillation, and the residue was dried under high vacuum. The resulting solid was ground to a powder with a mortar and pestle under a nitrogen atmosphere and quickly added to a 28% solution of aqueous ammonia at 0° C. The mixture was stirred briefly at 0° C. and then at ambient temperature for 3 h. The crude product was filtered, dried, and recrystallized from toluene-ethanol (1:1, v/v) to give 6.92 g (68.9%) of 5-bromonicotinamide, mp 210–213° C. (lit. mp 219–219.5° C., see C. V. Greco et al., *J. Heteocyclic Chem.* 7(4): 761 (1970)).

3-Amino-5-bromopyridine

Sodium hydroxide (2.50 g, 62.50 mmol) was added to a cold (0° C.), stirring suspension of calcium hypochlorite solution (1.53 g, 7.50 mmol of 70% solution) in water (35 mL). The mixture was stirred 15 min at 0° C. and filtered. The clarified filtrate was cooled and stirred in an ice-salt bath while 5-bromonicotinamide (3.03 g, 15.1 mmol) was added in one portion. The suspension was stirred 2 h at 0° C., warmed to ambient temperature, and heated on a steam bath for 1 h. After cooling, the mixture was extracted with $CHCl_3$ (2×50 mL). The combined $CHCl_3$ extracts were dried ($Na_2SO_4$), filtered, and concentrated on a rotary evaporator producing 1.42 g of a light-yellow solid. The aqueous layer was adjusted to pH 8 with 6M HCl solution and extracted with $CHCl_3$ (2×50 mL). The combined $CHCl_3$ extracts were dried ($Na_2SO_4$), filtered, and concentrated on a rotary evaporator, affording 0.98 g of a brown solid. Based upon TLC analysis (toluene-ethanol (3:1, v/v)), both crude products were combined to give 2.40 g which was dissolved in ethanol (10 mL) and filtered to remove a small amount of a light-yellow solid (80 mg, mp 225–227° C.). The filtrate was concentrated on a rotary evaporator, and the residue was dissolved in 2-propanol (6 mL), filtered, and cooled to 5° C. The resulting precipitate was filtered and dried to give a small amount of a tan solid (65 mg, mp 63–64° C.). The filtrate was concentrated on a rotary evaporator, and the residue was dissolved in toluene (5 mL), assisted by heating, and cooled to 5° C. The resulting precipitate was filtered and dried under vacuum to give 1.80 g of a brown, crystalline solid, mp 65–67° C. By concentrating the filtrate and cooling, a second crop of 0.27 g of a brown solid, mp 64–66° C. (lit. mp 69–69.5° C., see C. V. Greco et al., *J. Heteocyclic Chem.* 7(4): 761 (1970)) was obtained, bringing the total yield to 2.07 g (79.3%).

5-Bromo-3-isopropoxypyridine

A slurry of 5-amino-3-bromopyridine (1.29 g, 7.46 mmol) in 6M HCl solution (5 mL) was stirred 30 min at ambient temperature. The mixture was concentrated under high vacuum, and the residue was vacuum dried for 15 h at 50° C., affording a tan solid. The solid was slurried in 2-propanol (25 mL), and treated with isoamyl nitrite (1.70 g, 15.00 mmol). The mixture was stirred and heated under reflux for 1.5 h. The solution was concentrated by rotary evaporation, and the residue was partitioned between diethyl ether and 1M NaOH solution. The aqueous layer was separated and extracted with ether. The combined ether extracts were dried ($Na_2SO_4$), filtered, and concentrated by rotary evaporation producing an orange oil (2.03 g). The oil was purified by vacuum distillation, collecting the fraction with bp 105–115° C. at 9 mm Hg. The distilled product was further purified by column chromatography on silica gel, eluting with 10→20% (v/v) diethyl ether in hexane. Selected fractions, based upon TLC analysis ($R_f$ 0.40 in hexane-ether, (4:1, v/v)) were combined and concentrated by rotary evaporation to give 566.0 mg (35.2%) of a clear, colorless oil.

(4E)-N-Methyl-N-(tert-butoxycarbonyl)-5-(5-isopropoxy-3-pyridyl)-4-penten-2-amine Under a nitrogen atmosphere, a mixture of 5-bromo-3-isopropoxypyridine (847.0 mg, 3.92 mmol), N-methyl-N-(tert-butoxycarbonyl)-4-penten-2-amine (784.7 mg, 3.94 mmol), palladium(II) acetate (9.0 mg, 0.04 mmol), tri-o-tolylphosphine (50.0 mg, 0.16 mmol), triethylamine (0.73 g, 7.21 mmol), and anhydrous acetonitrile (2 mL) was stirred and heated under reflux at 80° C. for 20 h. The mixture, containing solids was cooled, diluted with water (10 mL), and extracted with $CHCl_3$ (3×10 mL). The combined $CHCl_3$ extracts were dried ($Na_2SO_4$), filtered, and concentrated by rotary evaporation to give an oily residue (1.56 g). The crude product was purified by column chromatography on silica gel, eluting with 25→40% (v/v) ethyl acetate in hexane. Selected fractions containing the product were combined and concentrated to give 1.15 g (87.8%) of a light-amber oil.

(4E)-N-Methyl-5-(5-isopropoxy-3-pyridyl)-4-penten-2-amine

Under a nitrogen atmosphere, a cold (0–5° C.), stirring solution of (4E)-N-methyl-N-(tert-butoxycarbonyl)-5-(5- isopropoxy-3-pyridyl)-4-penten-2-amine (150.0 mg, 0.45 mmol) in anisole (2.25 mL) was treated with trifluoroacetic acid (1.49 g, 13.79 mmol) in one portion. The resulting solution was stirred for 15 min at 0–5° C. TLC analysis on silica gel (EtOAc-hexane (3:1, v/v) and $CH_3OH$—$Et_3N$ (97.5:2.5, v/v)) indicated almost complete reaction. After stirring for an additional 15 min, the solution was concentrated on a rotary evaporator, followed by further drying under vacuum at 0.5 mm Hg to give 278 mg of a dark-yellow oil. The oil was cooled (0–5° C.), basified with 10% NaOH solution (2 mL) to pH 12, and saturated NaCl solution (5 mL) was added. The mixture was extracted with $CHCl_3$ (5×3 mL). The combined $CHCl_3$ extracts were washed with saturated NaCl solution (5 mL), dried ($Na_2SO_4$), filtered, concentrated by rotary evaporation, followed by further drying at 0.5 mm Hg to give 104.7 mg of a light-yellow, slightly orange oil. The crude product was purified by column chromatography on silica gel (20 g), eluting with $CH_3OH$—$Et_3N$ (100:2, v/v). Selected fractions containing the product ($R_f$ 0.37) were combined and concentrated on a rotary evaporator to afford 72.3 mg of a yellow oil. The oil was dissolved in $CHCl_3$ (25 mL), and the $CHCl_3$ solution was dried ($Na_2SO_4$), filtered, concentrated by rotary evaporation, and vacuum dried to give 69.3 mg (66.2%) of a yellow oil.

(4E)-N-Methyl-5-(5-isopropoxy-3-pyridyl)-4-penten-2-amine Hemigalactarate (4E)-N-Methyl-5-(5-isopropoxy-3-pyridyl)-4-penten-2-amine (69.3 mg, 0.23 mmol) was dissolved in $CH_3OH$ (1.5 mL), assisted by heating. The warm solution was treated with galactaric acid (24.3 mg, 0.12 mmol), followed by water (0.3 mL). The resulting solution was warmed and filtered through glass wool to remove a few insoluble particles, washing the filter plug with 0.4 mL of a $CH_3OH$—$H_2O$ (4:1, v/v) solution. The filtrate was diluted with $CH_3OH$ (1.5 mL), and the light-yellow solution was stored at 5° C. for 15 h. No precipitate had formed; therefore, the solution was concentrated on a rotary evaporator. The resulting solids were triturated with anhydrous diethyl ether (3×6 mL). The product was dried under a stream of nitrogen, dried under high vacuum, followed by further vacuum drying at 45° C. for 15 h to afford 73.0 mg (93.1%) of an off-white powder, mp 144–146.5° C.

Sample No. 4 exhibits a log P of 2.957, and such a favorable log P value indicates that the compound has the capability of passing the blood-brain barrier. The sample exhibits a Ki of 10 nM. The low binding constant indicates that the compound exhibits good high affinity binding to certain CNS nicotinic receptors.

Sample No. 4 exhibits an $EC_{50}$ value of 100 nM and an $E_{max}$ value of 57% for dopamine release, indicating that the compound effectively induces neurotransmitter release thereby exhibiting known nicotinic pharmacology. The sample exhibits an $EC_{50}$ value of 100 nM and an $E_{max}$ value of 60% in the rubidium ion flux assay, indicating that the compound effectively induces activation of CNS nicotinic receptors.

Sample No. 4 exhibits an $E_{max}$ of 15% (at a concentration of 100 $\mu$M) at muscle-type receptors, indicating that the compound does not significantly induce activation of muscle-type receptors. The sample exhibits an $E_{max}$ of 36% (at a concentration of 100 $\mu$M) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglion effects to any significant degree. The compound begins to cause muscle effects and ganglion effects only when employed in amounts greater than those required to activate rubidium ion flux and dopamine release, thus indicating a lack of undesirable side effects in subjects receiving administration of this compound.

EXAMPLE 11

Sample No. 5 is (2R)-(4E)-N-methyl-5-(5-isopropoxy-3-pyridyl)-4-penten-2-amine hemigalactarate, which was prepared in accordance with the following techniques:

(2S)-4-Penten-2-ol (2S)-4-Penten-2-ol was prepared from (S)-(−)-propylene oxide using a procedure similar to that described for the preparation of (2R)-4-penten-2-ol from (R)-(+)-propylene oxide as detailed in A. Kalivretenos, J. K. Stille, and L. S. Hegedus, *J. Org. Chem.* 56: 2883 (1991). Thus, a 1.0M solution of vinylmagnesium bromide in THF (129 mL, 129.0 mmol) was slowly added to a suspension of copper(I) iodide (2.46 g, 12.92 mmol) in dry THF (40 mL, distilled from sodium and benzophenone) at −25° C. After stirring 5 min, a solution of (S)-(−)-propylene oxide (5.00 g, 86.1 mmol) in dry THF (5 mL) was added. The mixture was allowed to warm to −10° C. and placed in a freezer at 0° C. for 12 h. The mixture was stirred for an additional 1 h at 0° C. and poured into a mixture of saturated ammonium chloride solution (100 mL) and ice (100 g). The mixture was stirred for 4 h and extracted with ether (3×100 mL). The combined ether extracts were dried ($K_2CO_3$), filtered, and concentrated under reduced pressure by rotary evaporation at 0° C. The resulting brown oil was vacuum distilled to yield 5.86 g (79.1%) of a colorless distillate, bp 37–39° C. at 9 mm Hg.

(2S)-(4E)-5-(5-Isopropoxy-3-pyridyl)-4-penten-2-ol

A mixture of 5-bromo-3-isopropoxypyridine (12.56 g, 58.13 mmol), (2S)-4-penten-2-ol (5.00 g, 58.05 mmol), palladium(II) acetate (130 mg, 0.58 mmol), tri-o-tolylphosphine (706 mg, 2.32 mmol), triethylamine (35 mL, 252 mmol) and acetonitrile (35 mL) were heated in a sealed glass tube at 130–140° C. for 8 h. The reaction mixture was cooled to ambient temperature. The solvent was removed under reduced pressure on a rotary evaporator. Water (50 mL) was added and the mixture was extracted with chloroform (3×50 mL). The combined chloroform extracts were dried ($K_2CO_3$), filtered, and concentrated by rotary evaporation. The crude product was purified by column chromatography over silica gel, eluting with chloroform-acetone (95:5, v/v). Selected fractions were combined and concentrated by rotary evaporation, producing 7.80 g (60.7%) of a pale-yellow oil.

(2S)-(4E)-5-(5-Isopropoxy-3-pyridyl)-4-penten-2-ol p-Toluenesulfonate

Under a nitrogen atmosphere, p-toluenesufonyl chloride (11.45 g, 60.06 mmol) was added to a stirring solution of (2S)-(4E)-5-(5-isopropoxy-3-pyridyl)-4-penten-2-ol (7.00 g, 31.63 mmol) in dry triethylamine (30 mL) at 0° C. After stirring and warming to ambient temperature over 18 h, the mixture was concentrated on a rotary evaporator. The crude product was stirred with saturated $NaHCO_3$ solution (100 mL) for 1 hour and extracted with chloroform (3×50 mL). The combined chloroform extracts were dried ($K_2CO_3$), filtered, and concentrated by rotary evaporation to afford 10.00 g (84.2%) as a dark-brown oil, which was used without further purification.

(2R)-(4E)-N-Methyl-5-(5-isopropoxy-3-pyridyl)-4-penten-2-amine

A mixture of (2S)-(4E)-5-(5-isopropoxy-3-pyridyl)-4-penten-2-ol p-toluenesulfonate (10.00 g, 26.63 mmol) and methylamine (50 mL, 2.0M solution in THF) was heated at 100° C. for 10 h in a sealed glass tube. The mixture was cooled to ambient temperature and concentrated under reduced pressure on a rotary evaporator. The crude product was treated with saturated $NaHCO_3$ solution (50 mL) and extracted with chloroform (4×50 mL). The combined chloroform extracts were dried ($K_2CO_3$), filtered, and concentrated by rotary evaporation to afford a dark-brown oil (3.50 g). The crude product was purified by repeated (twice) column chromatography on silica gel, eluting with chloroform-methanol (95:5, v/v). Selected fractions were combined, concentrated by rotary evaporation affording a light-brown oil (2.50 g). The oil was further purified by vacuum distillation using a short-path distillation apparatus, collecting 2.05 g (32.9%) of a colorless oil, bp 98–100° C. at 0.04 mm Hg.

(2R)-(4E)-N-Methyl-5-(5-isopropoxy-3-pyridyl)-4-penten-2-amine Hemigalactarate

Galactaric acid (314.0 mg, 1.49 mmol) was dissolved in 2-propanol (10 mL) and water (~1 mL), assisted by heating and sonicating over a period of 10 min. A solution of (2R)-(4E)-N-methyl-5-(5-isopropoxy-3-pyridyl)-4-penten-2-amine (700.3 mg, 2.99 mmol) in 2-propanol (10 mL) was then added, followed by additional sonicating and heating at 60° C. for 10 min. The hot solution was filtered to remove some insoluble material. The solvent was removed on a rotary evaporator; the resulting light-brown syrup was dissolved in dry 2-propanol (5 mL) and cooled at 4° C. The resulting precipitate was filtered and dried under high vacuum to yield 657 mg (64.8%) of an off-white, crystalline powder, mp 150–153° C.

Sample No. 5 exhibits a log P of 2.957, and such a favorable log P value indicates that the compound has the capability of passing the blood-brain barrier. The sample exhibits a Ki of 62 nM. The low binding constant indicates that the compound exhibits good high affinity binding to certain CNS nicotinic receptors.

Sample No. 5 exhibits an $EC_{50}$ value of 634 nM and an $E_{max}$ value of 38% for dopamine release, indicating that the compound effectively induces neurotransmitter release thereby exhibiting known nicotinic pharmacology. The sample exhibits an $EC_{50}$ value of 88 nM and an $E_{max}$ value of 14% in the rubidium ion flux assay, indicating that the compound induces activation of CNS nicotinic receptors.

Sample No. 5 exhibits an $E_{max}$ of 0% (at a concentration of 100 μM) at muscle-type receptors, indicating that the compound does not induce activation of muscle-type receptors. The sample exhibits an $E_{max}$ of 14% (at a concentration of 100 μM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglia effects to any significant degree.

EXAMPLE 12

Sample No. 6 is (2S)-(4E)-N-methyl-5-(5-isopropoxy-3-pyridyl)-penten-2-amine hemigalactarate, which was prepared in accordance with the following techniques:

(2R)-4-Penten-2-ol (2R)-4-Penten-2-ol was prepared in 82.5% yield from (R)-(+)-propylene oxide according to procedures set forth in A. Kalivretenos, J. K. Stille, and L. S. Hegedus, *J. Org. Chem.* 56: 2883 (1991).

(2R)-(4E)-5-(5-Isopropoxy-3-pyridyl)-4-penten-2-ol

A mixture of 5-bromo-3-isopropoxypyridine (10.26 g, 47.50 mmol), (2R)-4-penten-2-ol (4.91 g, 57.00 mmol), palladium(II) acetate (106 mg, 0.47 mmol), tri-o-tolylphosphine (578 mg, 1.90 mmol), triethylamine (28.46 mL, 204.25 mmol), and acetonitrile (30 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate, filtered, and concentrated by rotary evaporation to give a pale-yellow oil (8.92 g, 85.0%).

(2R)-(4E)-5-(5-Isopropoxy-3-pyridyl)-4-penten-2-ol p-Toluenesulfonate

To a stirred solution of (2R)-(4E)-5-(5-isopropoxy-3-pyridyl)-4-penten-2-ol (8.50 g, 38.46 mmol) in dry pyridine (30 mL) at 0° C. was added p-toluenesulfonyl chloride (14.67 g, 76.92 mmol). The reaction mixture was stirred for 24 h at ambient temperature. The pyridine was removed by rotary evaporation. Toluene (50 mL) was added to the residue and removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation to yield a dark-brown, viscous oil (11.75 g, 81.5%).

(2S)-(4E)-N-Methyl-5-(5-isopropoxy-3-pyridyl)-4-penten-2-amine

A mixture of (2R)-(4E)-5-(5-isopropoxy-3-pyridyl)-4-penten-2-ol p-toluenesulfonate (11.00 g, 29.33 mmol), methylamine (200 mL, 40% solution in water), and ethyl alcohol (10 mL) was stirred at ambient temperature for 18 h. The resulting solution was extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-methanol (7:3, v/v). Selected fractions were combined and concentrated by rotary evaporation, producing an oil. Further purification by vacuum distillation furnished 2.10 g (31.0%) of a colorless oil, bp 90–100° C. at 0.5 mm Hg.

(2S)-(4E)-N-Methyl-5-(5-isopropoxy-3-pyridyl)-4-penten-2-amine Hemigalactarate (2S)-(4E)-N-Methyl-5-(5-isopropoxy-3-pyridyl)-4-penten-2-amine (2.00 g, 8.55 mmol) was dissolved in ethyl alcohol (20 mL), assisted by warming to 70° C. The warm solution was treated with galactaric acid (900 mg, 4.27 mmol) in one portion, followed by the dropwise addition of water (0.5 mL). The solution was filtered while hot to remove some insoluble material. The filtrate was allowed to cool to ambient temperature. The resulting crystals were filtered, washed with anhydrous diethyl ether, and dried under vacuum at 40° C. to yield a white, crystalline powder (750 mg, 26.0%), mp 140–143° C.

Sample No. 6 exhibits a log P of 2.957, and such a favorable log P value indicates that the compound has the capability of passing the blood-brain barrier. The sample exhibits a Ki of 11 nM. The low binding constant indicates that the compound exhibits good high affinity binding to certain CNS nicotinic receptors.

Sample No. 6 exhibits an $EC_{50}$ value of 106 nM and an $E_{max}$ value of 85% for dopamine release, indicating that the compound effectively induces neurotransmitter release thereby exhibiting known nicotinic pharmacology. The sample exhibits an $EC_{50}$ value of 220 nM and an $E_{max}$ value of 58% in the rubidium ion flux assay, indicating that the compound effectively induces activation of CNS nicotinic receptors.

Sample No. 6 exhibits an $E_{max}$ of 0% (at a concentration of 100 μM) at muscle-type receptors, indicating that the compound does not induce activation of muscle-type receptors. The sample exhibits an $E_{max}$ of 0% (at a concentration of 100 μM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle or ganglia effects to any significant degree.

EXAMPLE 13

Sample No. 7 is (4E)-N-methyl-5-(5-bromo-3-pyridyl)-4-penten-2-amine, which was prepared in accordance with the following techniques:

(4E)-5-(5-Bromo-3-pyridyl)-4-penten-2-ol A mixture of 3,5-dibromopyridine (23.60 g, 100.0 mmol), 4-penten-2-ol (10.8 g, 125.0 mmol), palladium(II) acetate (230 mg, 1.02 mmol), tri-o-tolylphosphine (1.20 g, 3.94 mmol), triethylamine (29.7 mL, 213.45 mmol), and acetonitrile (40 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate and filtered. Removal of solvent by rotary evaporation, followed by column chromatography over silica gel eluting with acetone-chloroform (1:9, v/v) furnished 8.10 g (34.0%) of a pale-yellow oil.

(4E)-N-Methyl-5 -(5-bromo-3-pyridyl)-4-penten-2-amine

To a stirring solution of (4E)-5-(5-bromo-3-pyridyl)-4-penten-2-ol (3.14 g, 13.0 mmol) in dry pyridine (30 mL) at 0° C. was added p-toluenesulfonyl chloride (3.71 g, 19.5 mmol). The reaction mixture was stirred for 24 h at ambient temperature. The pyridine was removed by rotary evaporation. Toluene (50 mL) was added to the residue and subsequently removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation to give (4E)-5-(5-bromo-3-pyridyl)-4-penten-2-ol p-toluenesulfonate. The resulting tosylate was treated with excess methylamine (40% solution in water), ethyl alcohol (10 mL), and stirred at ambient temperature for 18 h. The resulting solution was extracted with chloroform (3×100 mL). The combined chloroform extracts were dried over sodium sulfate and filtered. Removal of solvent by rotary evaporation followed by column chromatography over silica gel eluting with chloroform-methanol (95:5, v/v) produced 1.50 g (45.0%) of a pale-yellow oil.

Sample No. 7 exhibits a log P of 2.026, and such a favorable log P value indicates that the compound has the capability of passing the blood-brain barrier. The sample exhibits a Ki of 284 nM, indicating that the compound exhibits binding to certain CNS nicotinic receptors.

Sample No. 7 exhibits an $EC_{50}$ value of 202 nM and an $E_{max}$ value of 18% for dopamine release, indicating that the compound induces neurotransmitter release thereby exhibiting known nicotinic pharmacology. The sample exhibits an $E_{max}$ value of 0% in the rubidium ion flux assay, indicating that the compound exhibits selective effects at certain CNS nicotinic receptors.

Sample No. 7 exhibits an $E_{max}$ of 6% (at a concentration of 100 μM) at muscle-type receptors, indicating that the compound does not induce activation of muscle-type receptors. The sample exhibits an $E_{max}$ of 8% (at a concentration of 100 μM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle or ganglia effects to any significant degree.

EXAMPLE 14

Sample No. 8 is (4E)-N-methyl-5-(5-methoxy-3-pyridyl)-4-penten-2-amine hemigalactarate, which was prepared in accordance with the following techniques:

5-Bromo-3-methoxypyridine

A mixture of 3,5-dibromopyridine (20.00 g, 84.42 mmol), sodium methoxide (11.40 g, 211.06 mmol), and copper powder (1 g, 5% by weight of 3,5-dibromopyridine) in dry methanol was heated in a sealed glass tube at 150° C. for 14 h. The reaction mixture was cooled to ambient temperature and extracted with diethyl ether (4×200 mL). The combined ether extracts were dried over sodium sulfate, filtered, and concentrated by rotary evaporation. The crude product was purified by column chromatography over aluminum oxide, eluting with ethyl acetate-hexane (1:9, v/v). Selected fractions were combined and concentrated by rotary evaporation, producing 9.40 g (59.5%) of a colorless oil, which tended to crystallize upon cooling.

(4E)-5-(5-Methoxy-3-pyridyl)-4-penten-2-ol

A mixture of 5-bromo-3-methoxypyridine (4.11 g, 21.86 mmol), 4-penten-2-ol (2.25 g, 26.23 mmol), palladium(II) acetate (49 mg, 0.22 mmol), tri-o-tolylphosphine (266 mg, 0.87 mmol), triethylamine (13.71 mL, 98.37 mmol), and acetonitrile (15 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate, filtered, and concentrated by rotary evaporation to give 3.53 g (70.3%) of a pale-yellow oil.

(4E)-5-(5-Methoxy-3-pyridyl)-4-penten-2-ol p-Toluenesulfonate

To a stirred solution of (4E)-5-(5-methoxy-3-pyridyl)-4-penten-2-ol (3.50 g, 18.13 mmol) in dry pyridine (15 mL) at 0° C. was added p-toluenesulfonyl chloride (6.91 g, 36.27 mmol). The reaction mixture was stirred for 24 h at ambient temperature. The pyridine was removed by rotary evaporation. Toluene (50 mL) was added to the residue and subsequently removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation to give 5.25 g (83.5%) of a dark-brown, viscous oil.

(4E)-N-Methyl-5-(5-methoxy-3-pyridyl)4-penten-2-amine

A mixture of (4E)-5-(5-methoxy-3-pyridyl)4-penten-2-ol p-toluenesulfonate (5.00 g, 14.41 mmol), methylamine (150 mL, 40% solution in water), and ethyl alcohol (10 mL) was stirred at ambient temperature for 18 h. The resulting solution was extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-methanol (7:3, v/v). Selected fractions were combined and concentrated by rotary evaporation, producing an oil. Further purification by vacuum distillation furnished 1.25 g (41.8%) of a colorless oil, bp 90–100° C. at 0.5 mm Hg.

(4E)-N-Methyl-5-(5-methoxy-3-pyridyl)-4-penten-2-amine Hemigalactarate (4E)-N-Methyl-5-(5-methoxy-3-pyridyl)4-penten-2-amine (1.20 g, 5.83 mmol) was dissolved in ethyl alcohol (20 mL), assisted by warming to 60° C. The warm solution was treated with galactaric acid (610 mg, 2.91 mmol) in one portion, followed by dropwise addition of water (0.5 mL). The solution was filtered while hot to remove some insoluble material. The filtrate was allowed to cool to ambient temperature. The resulting crystals were filtered, washed with anhydrous diethyl ether, and dried under vacuum at 40° C. to yield 1.05 g (58.0%) of a white, crystalline powder, mp 143–145° C.

Sample No. 8 exhibits a log P of 2.025, and such a favorable log P value indicates that the compound has the capability of passing the blood-brain barrier. The sample exhibits a Ki of 22 nM. The low binding constant indicates that the compound exhibits good high affinity binding to certain CNS nicotinic receptors.

Sample No. 8 exhibits an $EC_{50}$ value of 5000 nM and an $E_{max}$ value of 110% for dopamine release, indicating that the compound effectively induces neurotransmitter release thereby exhibiting known nicotinic pharmacology.

Sample No. 8 exhibits an $E_{max}$ of 10% (at a concentration of 100 $\mu$M) at muscle-type receptors, indicating that the compound does not induce activation of muscle-type receptors. The sample exhibits an $E_{max}$ of 2% (at a concentration of 100 $\mu$M) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but do not show undesirable muscle or ganglion effects to any significant degree.

EXAMPLE 15

Sample No. 9 is (4E)-N-methyl-5-(5-ethoxy-3-pyridyl)-4-penten-2-amine hemigalactarate, which was prepared in accordance with the following techniques:

5-Bromo-3-ethoxypyridine

Under a nitrogen atmosphere, sodium (4.60 g, 200.0 mmol) was added to absolute ethanol (100 mL) at 0–5° C., and the stirring mixture was allowed to warm to ambient temperature over 18 h. To the resulting solution was added 3,5-dibromopyridine (31.50 g, 133.0 mmol), followed by DMF (100 mL). The mixture was heated at 70° C. for 48 h. The brown mixture was cooled, poured into water (600 mL), and extracted with ether (3×500 mL). The combined ether extracts were dried ($Na_2SO_4$), filtered, and concentrated by rotary evaporation, producing 46.70 g of an oil. Purification by vacuum distillation afforded 22.85 g (85.0%) of an oil, bp 89–90° C. at 2.8 mm Hg, (lit. bp 111° C. at 5 mm Hg, see K. Clarke et al., *J. Chem. Soc.* 1885 (1960)).

(4E)-N-Methyl-N-(tert-butoxycarbonyl)-5-(5-ethoxy-3-pyridyl)-4-penten-2-amine

Under a nitrogen atmosphere, a mixture of 5-bromo-3-ethoxypyridine (1.20 g, 5.94 mmol), N-methyl-N-(tert-butoxycarbonyl)-4-penten-2-amine (1.18 g, 5.94 mmol), palladium(II) acetate (13.5 mg, 0.06 mmol), tri-o-tolylphosphine (73.1 mg, 0.24 mmol), triethylamine (1.5 mL, 10.8 mmol), and anhydrous acetonitrile (3 mL) was stirred and heated under reflux at 80–85° C. for 28 h. The resulting mixture, containing beige solids, was cooled to ambient temperature, diluted with water (20 mL), and extracted with $CHCl_3$ (3×20 mL). The combined light-yellow $CHCl_3$ extracts were dried ($Na_2SO_4$), filtered, concentrated by rotary evaporation, and vacuum dried producing a yellow oil (1.69 g). The crude product was purified by column chromatography on silica gel (100 g), eluting with ethyl acetate-hexane (1:1, v/v). Selected fractions containing the product ($R_f$ 0.20) were combined, concentrated by rotary evaporation, and the residue was vacuum dried to give 0.67 g (35.2%) of a light-yellow oil.

(4E)-N-Methyl-5-(5-ethoxy-3-pyridyl)-4-penten-2-amine

Under a nitrogen atmosphere, a cold (0–5° C.), stirring solution of (4E)-N-methyl-N-(tert-butoxycarbonyl)-5-(5-ethoxy-3-pyridyl)-4-penten-2-amine (0.67 g, 2.09 mmol) in anisole (10 mL) was treated dropwise over 30 min with trifluoroacetic acid (10.40 g, 91.17 mmol). The resulting solution was stirred for 45 min at 0–5° C. and was then concentrated by rotary evaporation. The light-yellow oil was further dried under high vacuum at 0.5 mm Hg. The resulting oil was cooled (0–5° C.), basified with 10% NaOH solution (10 mL), treated with saturated NaCl solution (7.5 mL), and extracted with $CHCl_3$ (4×10 mL). The combined light-yellow $CHCl_3$ extracts were washed with saturated NaCl solution (20 mL), dried ($Na_2SO_4$), filtered, concentrated by rotary evaporation, followed by further drying at 0.5 mm Hg producing a brown oil (0.46 g). The crude product was purified by column chromatography on silica gel (56 g), eluting with $CH_3OH$—$Et_3N$ (98:2, v/v). Selected fractions containing the product ($R_f$ 0.35) were combined and concentrated on a rotary evaporator. The residue was dissolved in $CHCl_3$, and the $CHCl_3$ solution was dried ($Na_2SO_4$), filtered, concentrated by rotary evaporation, and vacuum dried to give 327.5 mg (71.0%) of a light-yellow oil.

(4E)-N-Methyl-5-(5-ethoxy-3-pyridyl)-4-penten-2-amine Hemigalactarate

To a solution of (4E)-N-methyl-5-(5-ethoxy-3-pyridyl)-4-penten-2-amine (151.4 mg, 0.68 mmol) in absolute ethanol (2.3 mL) was added galactaric acid (72.2 mg, 0.34 mmol). Water (0.5 mL) was added dropwise while gently warming the light-brown solution. The solution was filtered through glass wool to remove a few insoluble particles, washing the filter plug with ethanol-water (4:1, v/v) (1 mL). The filtrate was diluted with ethanol (3.4 mL), cooled to ambient temperature, and further cooled at 5° C. for 18 h. Because no precipitate had formed, the solution was concentrated on a rotary evaporator. The resulting solids were dried under high vacuum and recrystallized from 2-propanol-water. After cooling at 5° C. for 48 h the product was filtered, washed with cold 2-propanol, and vacuum dried at 45° C. for 6 h. Further vacuum drying at ambient temperature for 18 h afforded 168 mg (76.1%) of a white to off-white powder, mp 141–143.5° C.

Sample No. 9 exhibits a log P of 2.556, and such a favorable log P value indicates that the compound has the capability of passing the blood-brain barrier. The sample exhibits a Ki of 15 nM. The low binding constant indicates that the compound exhibits good high affinity binding to certain CNS nicotinic receptors.

Sample No. 9 exhibits an $EC_{50}$ value of 520 nM and an $E_{max}$ value of 85% for dopamine release, indicating that the compound effectively induces neurotransmitter release thereby exhibiting known nicotinic pharmacology. The sample exhibits an $E_{max}$ value of 0% in the rubidium ion flux assay, indicating that the compound exhibits selective effects at certain CNS nicotinic receptors.

Sample No. 9 exhibits an $E_{max}$ of 21% (at a concentration of 100 $\mu$M) at muscle-type receptors, indicating that the compound does not induce activation of muscle-type receptors. The sample exhibits an $E_{max}$ of 9% (at a concentration of 100 $\mu$M) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle or ganglia effects to any significant degree.

EXAMPLE 16

Sample No. 10 is (4E)-N-methyl-5-(6-amino-5-methyl-3-pyridyl)-4-penten-2-amine, which was prepared in accordance with the following techniques:

(4E)-N-Methyl-N-(tert-butoxycarbonyl)-5-(6-amino-5-methyl-3-pyridyl)-4-penten-2-amine A mixture of 2-amino-5-bromo-3-methylpyridine (1.41 g, 7.53 mmol), N-methyl-N-(tert-butoxycarbonyl)-4-penten-2-amine (1.50 g, 7.53 mmol), palladium(II) acetate (33.8 mg, 0.15 mmol), tri-o-tolylphosphine (183.2 mg, 0.60 mmol), triethylamine (4.50 mL, 32.3 mmol), and anhydrous acetonitrile (8 mL) was stirred and heated at 130–132° C. in a sealed glass tube for 18 h. The mixture was further heated at 140° C. for 84 h. The resulting dark-brown solution was cooled to ambient temperature and concentrated by rotary evaporation. The residue was diluted with water (25 mL) and extracted with $CH_2Cl_2$ (3×25 mL). The combined $CH_2Cl_2$ extracts were dried ($Na_2SO_4$), filtered, concentrated by rotary evaporation, and vacuum dried producing a dark-brown oil (2.84 g). The crude product was purified by column chromatography on silica gel (135 g), eluting with ethyl acetate-hexane (3:1, v/v) to remove impurities, followed by elution with $CH_3OH$—$Et_3N$ (98:2, v/v) to collect the product. Fractions containing the product ($R_f$ 0.70) were combined and dissolved in $CHCl_3$. The $CHCl_3$ solution was dried ($Na_2SO_4$), filtered, concentrated by rotary evaporation, and vacuum dried to give 1.11 g (48.4%) of an amber-brown oil.

(4E)-N-Methyl-5-(6-amino-5-methyl-3-pyridyl)-4-penten-2-amine

Under a nitrogen atmosphere, trifluoroacetic acid (17.76 g, 155.76 mmol) was added dropwise, via addition funnel, over 30 min to a cold (0–5° C.), stirring solution of (4E)-N-methyl-N-(tert-butoxycarbonyl)-5-(6-amino-5-methyl-3-pyridyl)-4-penten-2-amine (1.11 g, 3.47 mmol) in anisole (15 mL). The resulting solution was stirred for 45 min at 0–5° C. and was then concentrated by rotary evaporation. The viscous, brown oil was further dried under high vacuum for 18 h. The crude product was cooled (0–5° C.), basified with 10% NaOH solution (10 mL), treated with saturated NaCl solution (10 mL), and extracted with $CHCl_3$ (5×10 mL). The combined $CHCl_3$ extracts were dried ($Na_2SO_4$), filtered, concentrated by rotary evaporation, followed by further drying under high vacuum yielding a dark-brown oil. The crude product was purified by column chromatography on silica gel (50 g), eluting with $CHCl_3$—$CH_3OH$—$Et_3N$ (4:1:1, v/v/v). Selected fractions containing the product ($R_f$ 0.13) were combined and concentrated by rotary evaporation, and the residue was re-chromatographed on silica gel (50 g) eluting with $CHCl_3$—$CH_3OH$ (7:3, v/v). Fractions containing the product ($R_f$ 0.12) were combined and concentrated by rotary evaporation. The residue was dissolved in $CHCl_3$, and the $CHCl_3$ solution was dried ($Na_2SO_4$), filtered, concentrated by rotary evaporation, and vacuum dried affording a yellow oil (0.087 g) which tended to crystallize. The semi-crystalline material was dissolved in a warm solution of hexane containing a small amount of ethyl acetate. The warm solution was decanted from an insoluble gum. The solution was allowed to cool to ambient temperature and was further cooled at 5° C. for 18 h. The resulting crystalline solids were collected, washed with hexane, and vacuum dried at 40° C. for 16 h. The yield was 30.8 mg (4.3%) of a light-yellow powder, mp 78–81° C.

Sample No. 10 exhibits a log P of 1.333, and such a favorable log P value indicates that the compound has the capability of passing the blood-brain barrier. The sample exhibits a Ki of 720 nM. The binding constant indicates that the compound exhibits high affinity binding to certain CNS nicotinic receptors.

Sample No. 10 exhibits an $EC_{50}$ value of 100000 nM and an $E_{max}$ value of 200% for dopamine release, indicating that the compound induces neurotransmitter release thereby exhibiting known nicotinic pharmacology.

Sample No. 10 exhibits an $E_{max}$ of 0% (at a concentration of 100 $\mu$M) at muscle-type receptors, indicating that the compound does not induce activation of muscle-type receptors. The sample exhibits an $E_{max}$ of 0% (at a concentration of 100 $\mu$M) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders.

EXAMPLE 17

Sample No. 11 is (4E)-N-methyl-5-(5-pyrimidinyl)-4-penten-2-amine hemigalactarate, which was prepared in accordance with the following techniques:

(4E)-N-Methyl-N-(tert-butoxycarbonyl)-5-(5-pyrimidinyl)-4-penten-2-ol

A glass pressure tube was charged with a mixture of 5-bromopyrimidine (1.28 g, 8.05 mmol), N-methyl-N-(tert-butoxycarbonyl)-4-penten-2-amine (1.60 g, 8.05 mmol), palladium(II) acetate (18.1 mg, 0.08 mmol), tri-o-tolylphosphine (98.6 mg, 0.32 mmol), triethylamine (3.00 mL, 21.5 mmol), and anhydrous acetonitrile (6 mL). The tube was flushed with nitrogen and sealed. The mixture was stirred and heated at 90° C. for 64 h, followed by further heating at 110° C. for 24 h. The resulting brown mixture was cooled to ambient temperature and concentrated by rotary evaporation. The brown residue was diluted with water (25 mL) and extracted with $CH_2Cl_2$ (3×25 mL). The combined $CH_2Cl_2$ extracts were dried ($Na_2SO_4$), filtered, concentrated by rotary evaporation, and vacuum dried producing a dark-brown oil (2.24 g). The crude product was purified by column chromatography on silica gel (120 g), eluting with ethyl acetate-hexane (3:1, v/v). Fractions containing the product ($R_f$ 0.21) were combined, concentrated by rotary evaporation, and vacuum dried to give 1.05 g (46.9%) of a light-yellow oil.

(4E)-N-Methyl-5-(5-pyrimidinyl)-4-penten-2-ol

Under a nitrogen atmosphere, a stirring solution of (4E)-N-methyl-N-(tert-butoxycarbonyl)-5-(5-pyrimidinyl)-4-penten-2-ol (881.2 mg, 3.18 mmol) in $CHCl_3$ (55 mL) was treated dropwise at ambient temperature with iodotrimethylsilane (1.41 g, 7.03 mmol). The resulting solution was stirred for 30 min. Methanol (55 mL) was added, and the solution was stirred for an additional 1 h and was concentrated by rotary evaporation. With ice-bath cooling, the residue was basified with 10% NaOH solution (10 mL), treated with saturated NaCl solution (10 mL), and extracted with $CHCl_3$ (8×10 mL). The combined $CHCl_3$ extracts were dried ($Na_2SO_4$), filtered, concentrated by rotary evaporation, followed by further drying under high vacuum producing a light-brown oil (0.50 g). The crude product was purified by column chromatography on silica gel (50 g), eluting with $CH_3OH$—$NH_4OH$ (20:1, v/v). Fractions containing the product ($R_f$ 0.43) were combined, concentrated by rotary evaporation, and the residue was dissolved in $CHCl_3$. The $CHCl_3$ solution was dried ($Na_2SO_4$), filtered, concentrated by rotary evaporation, and vacuum dried affording 306.4 mg (54.4%) of a light-amber oil.

(4E)-N-Methyl-5-(5-pyrimidinyl)-4-penten-2-amine Hemigalactarate

To a warm solution of (4E)-N-methyl-5-(5-pyrimidinyl)-4-penten-2-amine (258.6 mg, 1.46 mmol) in absolute ethanol (2.3 mL) was added galactaric acid (153.3 mg, 0.73 mmol). Water (0.8 mL) was added, and the solution was heated to near reflux until most of the solids dissolved. The solution was filtered through glass wool to remove a few white, insoluble particles, washing the filter plug with a warm solution of ethanol-water (4:1, v/v) (1.1 mL). The filtrate was diluted with ethanol (6.5 mL), cooled to ambient temperature, and further cooled at 5° C. for 48 h. The white precipitate was filtered, washed with cold ethanol, and vacuum dried at 40° C. for 18 h. The yield was 390.6 mg (94.8%) of a fluffy, white, crystalline powder, mp 164–167° C.

Sample No. 11 is determined to exhibit a log P of 0.571, and such a favorable log P value indicates that the compound has the capability of passing the blood-brain barrier. The sample exhibits a Ki of 179 nM. The low binding constant indicates that the compound exhibits good high affinity binding to certain CNS nicotinic receptors.

Sample No. 11 exhibits an $EC_{50}$ value of 1500 nM and an $E_{max}$ value of 80% for dopamine release, indicating that the compound effectively induces neurotransmitter release thereby exhibiting known nicotinic pharmacology. The sample exhibits an $EC_{50}$ value of 100000 nM and an $E_{max}$ value of 0% in the rubidium ion flux assay, indicating that the compound exhibits selective effects at certain CNS nicotinic receptors.

Sample No. II exhibits an $E_{max}$ of 0% (at a concentration of 100 µM) at muscle-type receptors, indicating that the compound does not induce activation of muscle-type receptors. The sample exhibits an $E_{max}$ of 13% (at a concentration of 100 µM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders.

The foregoing is illustrative of the present invention and is not to be construed as limiting thereof. The invention is defined by the following claims, with equivalents of the claims to be included therein.

What is claimed is:

1. A method for treating a CNS disorder comprising administering to a subject in need thereof an effective amount of a N-methyl-5-(5-pyrimidinyl)-4-penten-2-amine compound.

2. The method according to claim 1, wherein the compound is (4E)-N-methyl-5-(5-pyrimidinyl)-4-penten-2-amine.

3. The method according to claim 1, wherein the compound is (2S)-N-methyl-5-(5-pyrimidinyl)-4-penten-2-amine.

4. The method according to claim 1, wherein the compound is (2S)-(4E)-N-methyl-5-(5-pyrimidinyl)-4-penten-2-amine.

5. The method according to claim 1, wherein the CNS disorder is attention deficit disorder.

6. The method according to claim 1, wherein the CNS is selected from the group consisting of Parkinsonism, Parkinson's Disease, Tourette's Syndrome, schizophrenia, and senile dementia of the Alzheimers type.

7. The method according to claim 1, wherein the amount effective to treat said CNS disorder is between about 10 µg/kg of patient weight/24 hours and less than 100 µg/kg of patient weight/24 hours.

8. The method according to claim 1, wherein the amount effective to treat said CNS disorder is at least about 10 µg/patient/24 hours and does not exceed about 500 µg/patient/24 hours.

9. The method according to claim 1, wherein the effective amount is such that the subject does not experience a concentration of the compound in plasma which exceeds 500 ng/ml.

* * * * *